(12) United States Patent
Vatter et al.

(10) Patent No.: US 7,772,214 B2
(45) Date of Patent: Aug. 10, 2010

(54) EMULSION COSMETIC COMPOSITIONS COMPRISING AN EMULSIFYING CROSSLINKED SILOXANE ELASTOMER

(75) Inventors: Michael Lee Vatter, Okeana, OH (US); Jorge Max Sunkel, Cinciannti, OH (US); Curtis Bobby Motley, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 364 days.

(21) Appl. No.: 09/902,321

(22) Filed: Jul. 10, 2001

(65) Prior Publication Data

US 2002/0018760 A1 Feb. 14, 2002

Related U.S. Application Data

(60) Provisional application No. 60/217,061, filed on Jul. 10, 2000.

(51) Int. Cl.
- *A61K 8/89* (2006.01)
- *A61K 8/03* (2006.01)
- *A61K 8/04* (2006.01)
- *A61K 8/19* (2006.01)

(52) U.S. Cl. .................. 514/63; 424/401; 424/70.7; 424/63; 424/64; 514/844; 514/847; 514/937

(58) Field of Classification Search .............. 424/63, 424/64, 69, 70.7, 70.12, 70.31, 401, 70.9, 424/70.121; 514/844, 937, 847, 63; 574/438
See application file for complete search history.

(56) References Cited

U.S. PATENT DOCUMENTS

| | | |
|---|---|---|
| 3,843,601 A | 10/1974 | Bruner |
| 4,554,369 A | 11/1985 | Hill et al. |
| 4,588,617 A | 5/1986 | Oka |
| 4,720,353 A | 1/1988 | Bell |
| 4,742,142 A | 5/1988 | Shimizu et al. |
| 4,752,528 A | 6/1988 | Oka |
| 4,761,454 A | 8/1988 | Oba et al. |
| 4,780,145 A | 10/1988 | Mori et al. |
| 4,970,252 A | 11/1990 | Sakuta et al. |
| 4,980,167 A | 12/1990 | Harashima et al. |
| 4,983,388 A | 1/1991 | Kuwata et al. |
| 4,987,169 A | 1/1991 | Kuwata et al. |
| 5,128,431 A | 7/1992 | Riding et al. |
| 5,143,722 A | 9/1992 | Hollenberg et al. |
| 5,143,722 A | 9/1992 | Hollenberg et al. |
| 5,220,033 A | 6/1993 | Kamei et al. |
| 5,236,986 A | 8/1993 | Sakuta |
| 5,266,321 A | 11/1993 | Shukuzaki et al. |
| 5,280,019 A | 1/1994 | Kllimisch |
| 5,330,747 A | 7/1994 | Krzysik |
| 5,387,417 A | 2/1995 | Rentsch |
| 5,399,342 A | 3/1995 | Krzysik |
| 5,403,580 A | 4/1995 | Bujanowski et al. |
| 5,412,004 A | 5/1995 | Tachibana et al. |
| 5,512,272 A | 4/1996 | Krzysik |
| 5,599,533 A | 2/1997 | Stepniewski et al. |
| 5,628,989 A | 5/1997 | Harashima et al. |
| 5,654,362 A | 8/1997 | Schulz, Jr. et al. |
| 5,665,804 A | 9/1997 | Hill et al. |
| 5,721,026 A | 2/1998 | Feder et al. |
| 5,725,845 A | 3/1998 | Krog et al. |
| 5,750,123 A | 5/1998 | Znaiden et al. |
| 5,756,568 A | 5/1998 | Morita et al. |
| 5,760,116 A | 6/1998 | Kilgour et al. |
| 5,811,487 A | 9/1998 | Schulz, Jr. et al. |
| 5,833,973 A | 11/1998 | Dobkowski et al. |
| 5,837,793 A | 11/1998 | Harashima et al. |
| 5,849,314 A | 12/1998 | Dobkowski et al. |
| 5,853,711 A | 12/1998 | Nakamura et al. |
| 5,853,741 A | 12/1998 | Znaiden et al. |
| 5,854,336 A | 12/1998 | Divone, Sr. et al. |
| 5,859,069 A | 1/1999 | Yanagida |
| 5,871,761 A | 2/1999 | Kuwata et al. |
| 5,880,210 A | 3/1999 | Schulz, Jr. et al. |
| 5,889,108 A | 3/1999 | Zhang |
| 5,919,437 A | 7/1999 | Lee et al. |
| 5,919,468 A | 7/1999 | Bara |
| 5,922,308 A | 7/1999 | Brewster et al. |

(Continued)

FOREIGN PATENT DOCUMENTS

CA 1319306 6/1993

(Continued)

OTHER PUBLICATIONS

Hawley, G. G., The Condensed Chemical Dictionary, 10$^{th}$ Ed., Van Nostrand Reinhold Co., New York (1981) pp. 121, 385, 434 and 686.*

(Continued)

*Primary Examiner*—Gina C Yu
(74) *Attorney, Agent, or Firm*—Megan C. Hymore; S. Robert Chuey; Carl J. Roof

(57) ABSTRACT

The present invention relates to pigmented emulsion cosmetic compositions containing emulsifying silicone elastomers that provide a natural appearance to the skin upon application. In particular, these cosmetic compositions are formulated such that agglomeration of the pigment upon application to the skin is minimized.

13 Claims, No Drawings

U.S. PATENT DOCUMENTS

| | | |
|---|---|---|
| 5,929,164 A | 7/1999 | Zhang |
| 5,939,478 A | 8/1999 | Beck et al. |
| 5,942,215 A | 8/1999 | Edwards et al. |
| 5,945,471 A | 8/1999 | Morita et al. |
| 5,948,855 A | 9/1999 | Lin et al. |
| 5,969,035 A | 10/1999 | Meinhardt et al. |
| 5,972,314 A | 10/1999 | Crotty et al. |
| 5,977,280 A | 11/1999 | Kadlec et al. |
| 5,985,807 A | 11/1999 | Auguste et al. |
| 5,998,542 A | 12/1999 | Horne et al. |
| 6,013,247 A | 1/2000 | Bara et al. |
| 6,024,944 A | 2/2000 | Hansenne |
| 6,027,738 A | 2/2000 | Stepniewski et al. |
| 6,066,727 A | 5/2000 | Yamamoto et al. |
| 6,074,672 A | 6/2000 | Dobkowski et al. |
| 6,080,394 A | 6/2000 | Lin et al. |
| 6,083,900 A | 7/2000 | Auguste et al. |
| 6,103,250 A | 8/2000 | Brieva et al. |
| 6,358,500 B1 | 3/2002 | Simon |
| 6,379,682 B1 * | 4/2002 | Tchinnis et al. ............ 424/401 |
| 6,464,966 B1 | 10/2002 | Simon |
| 6,475,500 B2 | 11/2002 | Vatter et al. |
| 6,524,598 B2 | 2/2003 | Sunkel et al. |
| 6,696,049 B2 | 2/2004 | Vatter et al. |
| 2001/0041768 A1 | 11/2001 | Lorant |
| 2002/0159963 A1 | 10/2002 | Simon |

FOREIGN PATENT DOCUMENTS

| | | |
|---|---|---|
| EP | 0 295886 A2 | 12/1988 |
| EP | 0 499398 A2 | 8/1992 |
| EP | 0 542498 A2 | 5/1993 |
| EP | 0 545002 A1 | 6/1993 |
| EP | 0 608 989 A2 | 8/1994 |
| EP | 0 796883 A2 | 9/1997 |
| EP | 0 829253 A2 | 3/1998 |
| EP | 0 848029 A2 | 6/1998 |
| EP | 0 850643 A1 | 7/1998 |
| EP | 0 855178 A2 | 7/1998 |
| EP | 0 882753 A1 | 12/1998 |
| EP | 0 908175 A1 | 4/1999 |
| EP | 0 917870 A1 | 5/1999 |
| EP | 0 934959 A1 | 8/1999 |
| EP | 0 958856 A1 | 11/1999 |
| EP | 0 972 512 A1 | 1/2000 |
| EP | 0 985402 A1 | 3/2000 |
| EP | 1 010715 A1 | 6/2000 |
| EP | 1 062944 A1 | 12/2000 |
| EP | 1 064930 A1 | 1/2001 |
| EP | 1 068852 A1 | 1/2001 |
| EP | 0 779322 B1 | 2/2001 |
| EP | 1 097968 A1 | 5/2001 |
| EP | 1095 959 A2 | 5/2001 |
| FR | 2 768 926 A1 | 4/1999 |
| FR | 2779440 A1 | 12/1999 |
| JP | SHO 61-194009 A | 8/1986 |
| JP | HEI 1-207354 A | 8/1989 |
| JP | 2000-86427 | 3/1990 |
| JP | HEI 4-017162 A | 3/1992 |
| JP | KOKAI 5-139929 A | 6/1993 |
| JP | 5-178733 A | 7/1993 |
| JP | 5-178734 | 7/1993 |
| JP | 6-72826 A | 3/1994 |
| JP | 7-258027 A | 10/1995 |
| JP | 7-277924 A | 10/1995 |
| JP | 8-259419 A | 10/1996 |
| JP | 8-295620 | 11/1996 |
| JP | 8-319215 A | 12/1996 |
| JP | 8-319218 A | 12/1996 |
| JP | 9-67233 A | 3/1997 |
| JP | 9-136813 A | 5/1997 |
| JP | 9-151126 A | 6/1997 |
| JP | 9-175939 A | 7/1997 |
| JP | 9-175940 A | 7/1997 |
| JP | 9-175990 A | 7/1997 |
| JP | 9-301825 A | 11/1997 |
| JP | 9-315936 A | 12/1997 |
| JP | 9-323917 A | 12/1997 |
| JP | 9-328409 A | 12/1997 |
| JP | 10-45536 A | 2/1998 |
| JP | 10-120525 A | 5/1998 |
| JP | 10-130120 A | 5/1998 |
| JP | 10-167925 A | 6/1998 |
| JP | 10-182354 A | 7/1998 |
| JP | 10-236917 A | 9/1998 |
| JP | 11-21227 A | 1/1999 |
| JP | 11-29436 A | 2/1999 |
| JP | 11-71236 A | 3/1999 |
| JP | 11-92335 A | 4/1999 |
| JP | 11-158036 A | 6/1999 |
| JP | 11-180847 A | 7/1999 |
| JP | 11-193214 A | 7/1999 |
| JP | 2000-7549 A | 1/2000 |
| JP | 2000-103717 A | 4/2000 |
| JP | 2000-226316 A | 8/2000 |
| WO | WO 96/18374 A1 | 6/1996 |
| WO | WO 97/44010 A1 | 11/1997 |
| WO | WO 98/00098 A1 | 1/1998 |
| WO | WO 98/00102 A1 | 1/1998 |
| WO | WO 98/00103 A1 | 1/1998 |
| WO | WO 98/00104 A1 | 1/1998 |
| WO | WO 98/00105 A1 | 1/1998 |
| WO | WO 98/42307 A1 | 10/1998 |
| WO | WO 99/00400 A1 | 1/1999 |
| WO | WO 99/13859 A1 | 3/1999 |
| WO | WO 99/22696 A1 | 5/1999 |
| WO | WO 99/43297 A2 | 9/1999 |
| WO | WO 99/51192 A2 | 10/1999 |
| WO | WO 99/63953 A1 | 12/1999 |
| WO | WO 00/21493 A1 | 4/2000 |
| WO | WO 00/61076 A1 | 10/2000 |
| WO | WO 00/61084 A1 | 10/2000 |
| WO | WO 00/72817 A1 | 12/2000 |
| WO | WO 01/12133 A2 | 2/2001 |

OTHER PUBLICATIONS

Translation of EPO,908,175A1 (Rouquet et al.) Apr. 14, 1999.

* cited by examiner

EMULSION COSMETIC COMPOSITIONS COMPRISING AN EMULSIFYING CROSSLINKED SILOXANE ELASTOMER

CROSS REFERENCE TO RELATED APPLICATION

This application claims the benefit of U.S. Provisional Application No. 60/217,061, filed Jul. 10, 2000.

FIELD OF THE INVENTION

The present invention relates to pigmented emulsion cosmetic compositions containing emulsifying silicone elastomers that provide a natural appearance to the skin upon application. In particular, these cosmetic compositions are formulated such that agglomeration of the pigment upon application to the skin is minimized.

BACKGROUND OF THE INVENTION

Cosmetic products (e.g., foundation products) are typically applied to the entire face to mask perceived imperfections in skin texture (i.e., fine lines and wrinkles), pigmentation or vascularization. It is desirable for foundations to mask these imperfections and yet still allow for a natural appearance of the skin. In other words, consumers want good coverage from a foundation product, but do not want the appearance of too much make-up, i.e., cakey appearance.

Pigmented oil-in-water and water-in-oil emulsion cosmetic products are a popular type of cosmetic product available on the market today. These products are relatively inexpensive and are easy to apply to the skin. Moreover, the pigmented oil-in-water or water-in-oil emulsion foundation lends itself to variation in pigment type and level to give different degrees of color coverage.

However, it is believed that, in order to minimize the appearance of fine lines and wrinkles and to avoid a cakey appearance when utilizing a certain cosmetic products, it is important to deposit the pigment particle or solid particle from the cosmetic product uniformly of the skin. Unfortunately, the tendency of the solid particles is to agglomerate (i.e., flocculate) in the foundation product and, upon application of the foundation product to the skin, to collect in the fine lines and wrinkles or otherwise agglomerate on the skin, thereby accentuating, rather than minimizing the appearance of the fine lines, and further providing a cakey, unnatural appearance to the skin.

Preventing agglomeration (flocculation) of the solid particles in foundation products and upon application to the skin can be very difficult. One way to improve the stability of solid particles in foundation products is to "coat" the particle; in other words, adsorb certain materials onto the surface of the particle. See Driscoll, P., "Treated Pigments in Decorative Cosmetics", Cosmetics and toiletries, Vol. 104 (July 1989), pp 43-45. Foundation and other personal care products containing hydrophobically or hydrophilically coated pigments are know in the art (See, for example, Lee, J et al., Preparation of Ultra Fine $Fe_3O_4$ Particles by Precipitation in the Presence of PVA at High pH", J. Colloid Interface Sci., 177, p. 490 [1996] and European Patent Application 504,066, published Mar. 13, 1992). Unfortunately, the methods taught in the art for preventing agglomeration of pigment particles in product and when applied to skin are not sufficient to provide products which meet consumer needs with respect to the natural appearance of the skin.

Another problem associated with the use of solid particles relates to the size of the particle. Solid particles having a particle size greater than 20 microns are difficult to disperse within the droplet phase of emulsions typically regarded as stable emulsions since such emulsions typically have discontinuous phase droplets of droplet size less than 20 microns. The smaller droplets avoid the "buoyancy effect" (i.e., where the buoyancy force of the discontinuous phase droplet exceeds the viscous forces of the continuous phase) associated with droplets having droplet sizes greater than 20 microns. Additionally, the surfactants or emulsifiers typically used in such emulsions do not tend to provide the structurant properties necessary to support emulsions having larger sized droplets (i.e., greater than 20 microns).

It has now been found, however, that cosmetic products can be formulated wherein the agglomeration of solid particles contained therein is minimized and wherein the skin deposition control is improved using the technology hereinafter described. Specifically, it has been found that the use of emulsifying type elastomers aid in controlling agglomeration of solid particles dispersed within the discontinuous droplet phase and provide stable emulsions supporting discontinuous phase droplets having a particle size greater than 20 microns. Moreover, when the cosmetic products of the present invention are applied to the skin, solid particles having a broad particle size distribution are capable of being uniformly deposited on the skin. Without being limited by theory, these solid particles are delivered to the skin by means of emulsion droplets having a broad droplet size distribution. Specifically, the solid particles, even those having a particle size greater than 20 microns, are dispersed within and/or at the droplet interface of the emulsion system such that capillary-induced agglomeration of the particles is confined within the space or volume occupied by the droplet, thereby providing a more even distribution of the broad range particles on skin. Additionally, the droplets serve as a barrier preventing agglomeration as a result of application shear. Accordingly, good coverage of the skin and a natural appearance of the skin is provided.

Accordingly, one aspect of the present invention is to provide cosmetic compositions which control agglomeration or flocculation of pigments in the cosmetic product and when applied to skin.

Another aspect of the present invention is to provide improved distribution of pigments on skin.

Still another aspect of the present invention is to provide good coverage of the skin as well as retain the natural appearance of the skin.

These and other aspects of the present invention will become more readily apparent from consideration of the following summary and detailed description.

SUMMARY OF THE INVENTION

The present invention relates to stable multiphase emulsion compositions, comprising:

A.) a continuous phase, comprising:
   i.) an emulsifying crosslinked siloxane elastomer; and
   ii.) a solvent for the emulsifying crosslinked siloxane elastomer;

B.) at least one discontinuous phase, comprising:
   i.) solid particles wherein the discontinuous phase forms droplets having a droplet size distribution range of from about 0.1 microns to about 100 microns and wherein the solid particles are uniformly distributed on the skin independent of skin topography.

Also claimed herein are cosmetic compositions comprising:

(i) from about 0.1% to about 15% of crosslinked siloxane elastomer having an average particle size less than 20 microns;

(ii) from 10 to 80% of a solvent for the crosslinked siloxane elastomer;

(iii) optionally, from 0 to 50% of skin conditioning agent; and (iv) optionally, from above about 0 to about 95% of water wherein contain at least about 1% air.

DETAILED DESCRIPTION OF THE INVENTION

As used herein, the term "cosmetics" includes make-up, foundation, and skin care products. The term "make-up" refers to products that leave color on the face, including foundation, blacks and browns, i.e., mascara, concealers, eye liners, brow colors, eye shadows, blushers, lip colors, powders, solid emulsion compact, and so forth. Skin care products are those used to treat or care for, or somehow moisturize, improve, or clean the skin. Products contemplated by the phrase "skin care products" include, but are not limited to, adhesives, bandages, toothpaste, anhydrous occlusive moisturizers, antiperspirants, deodorants, personal cleansing products, powder laundry detergent, fabric softener towels, occlusive drug delivery patches, nail polish, powders, tissues, wipes, hair conditioners-anhydrous, shaving creams and the like. The term "foundation" refers to liquid, creme, mousse, pancake, compact, concealer or like product created or reintroduced by cosmetic companies to even out the overall coloring of the skin. Foundation is manufactured to work better over moisturized and/or oiled skin. The compositions of the present invention also provide good make-up removal. The compositions of the present invention are especially useful in removal make-up compositions such as that disclosed in U.S. Pat. No. 6,019,962 to Rabe et al., which patent is herein incorporated by reference in its entirety.

The term "ambient conditions" as used herein refers to surrounding conditions under about one atmosphere of pressure, at about 50% relative humidity, and at about 25° C., unless otherwise specified.

The term "opaque" refers to a composition that is impervious to visible light. An opaque composition lacks any degree of transparency.

The phrase "capillary-induced aggregation", means the aggregation of solid particles by the capillary forces by the continuous evaporation of interstitial liquid(s).

As used herein the term "comprising" means that the composition can contain other ingredients which are compatible with the composition and which preferably do not substantially disrupt the compositions of the present invention. The term encompasses the terms "consisting of" and "consisting essentially of".

Unless otherwise indicated, all percentages and ratios used herein are by weight of the total composition. All weight percentages, unless otherwise indicated, are on an actives weight basis. All measurements made are at 25° C., unless otherwise designated.

A. The Continuous Phase of the Emulsion Composition

An essential component of the present invention is a continuous phase. The emulsion compositions of the present invention are heterogeneous systems containing at least two immiscible liquids, one of which is dispersed in the other in the form of droplets. The immiscible liquids form phases when mixed, a continuous and at least one discontinuous phase. The discontinuous phase is referred to variously as the dispersed or internal phase, whereas the phase in which the dispersion occurs is referred to as the continuous or external phase. Preferred emulsions of the present invention contain an oily (fatty or lipophilic) and a non-oily phase. Any oil or oily like ingredient (i.e., fats, natural or synthetic oils such as vegetable or silicone oils) is useful in forming the oil or oily phase and are typically the oils/solvents useful in gelling emulsifying crosslinked siloxane elastomer described below. Preferably the oily or oil-like materials or components constitute the continuous phase of the present invention. The continuous phase preferably comprises from 1 to 95%, more preferably 1 to 50%, most preferably from 10 to 40%, optimally from 25 to 35% by weight.

i.) Emulsifying Crosslinked Siloxane Elastomer

The continuous phase of the present invention preferably contains a crosslinked organopolysiloxane elastomer gel comprising a partially or completely crosslinked organopolysiloxane elastomer and a solvent for the emulsifying crosslinked organopolysiloxane elastomer. The crosslinked organopolysiloxane elastomers can be either partially or completely cross-linked. They are generally emulsifiers. They can notably be chosen from the crosslinked polymers described in U.S. Pat. No. 5,412,004 (issued May 2, 1995); U.S. Pat. No. 5,837,793 (issued Nov. 17, 1998); and U.S. Pat. No. 5,811,487 (issued Sep. 22, 1998), all of which are herein incorporated by reference in their entirety. These organopolysiloxanes are obtained by the addition polymerization of the following compounds (I) and (II):

(I) an organohydrogen polysiloxane having formula (I):

$$R^1_a R^2_b H_c SiO_{(4-a-b-c)/2} \quad (1)$$

in which $R^1$ represents a substituted or unsubstituted alkyl, aryl or aralkyl group, comprising 1-18 carbon atoms, or a halogenated hydrocarbon group; $R^2$ represents a group:

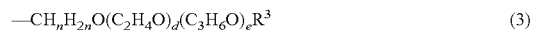

$$-CH_nH_{2n}O(C_2H_4O)_d(C_3H_6O)_e R^3 \quad (3)$$

in which $R^1$ is a hydrogen atom, a saturated aliphatic hydrocarbon group having 1-10 carbon atoms or a —(CO)—$R^5$ group where $R^5$ is a saturated aliphatic hydrocarbon group having 1-5 carbon atoms; d is a whole number from 2 to 200, and e is a whole number from 0 to 200, provided that d+e is a number in the range of 3 to 200, and n is a number in the range of 2 to 6, a is a value satisfying the inequality: $1.0 \leq a \leq 2.5$, b is a value satisfying the inequality: $0.001 \leq b \leq 1.0$ and c is a value satisfying the inequality: $0.001 \leq c \leq 1.0$;

or an organohydrogen polysiloxane represented by the following formula (2):

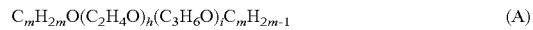

$$C_m H_{2m} O(C_2H_4O)_h (C_3H_6O)_i C_m H_{2m-1} \quad (A)$$

in which h is a whole number in the range of 2 to 200, I is a whole number in the range of 0 to 200, provided that h+i is a number in the range of 3 to 200, and m is a number in the range of 2 to 6, or an organopolysiloxane represented by the following formula (B):

$$R^1_j R^4_k SiO_{(4-j-k)/2} \quad (B)$$

in which R' has the same meaning as in formula (1), $R^4$ is a monovalent hydrocarbon group having an unsaturated aliphatic bond at the end and containing 2-10 carbon atoms, j is a value satisfying the inequality: $1.0 \leq j \leq 3.0$ and k is a value satisfying the inequality 0.001≦k≦1.5, or a mixture of the polyoxyalkylene having formula (A) or of the organopolysiloxane having formula (B), where at least one organohydrogen polysiloxane having formula (1) or at least one polyoxyalkylene having formula (A) is contained as an essential element of the addition polymerization.

It is preferred for the organopolysiloxane to be in a mixture with a silicone oil and/or polyol, and to be prepared directly in such a mixture. The silicone oil preferably has a viscosity equal to or less than 500 cSt at 25° C. According to an embodiment of the invention, the organopolysiloxane elastomer is prepared from 100 parts by weight of the constituents defined above and 3-200 parts by weight of a silicone oil having a viscosity equal to or less than 100 cSt at 25° C., and/or a polyol. The silicone oil can be a volatile or nonvolatile silicone oil or a mixture of a volatile silicone oil and a nonvolatile silicone oil.

The organopolysiloxanes of the invention are obtained, in particular, according to the protocol of Examples 3, 4, and of the document EP-A545002 (or U.S. Pat. No. 5,421,004) and from the examples of the document U.S. Pat. No. 5,811,487.

The organopolysiloxanes of the composition of the invention contain one or more oxyalkylenated group(s) and in particular oxyethylenated (OE) group(s), for example, 1-40 oxyalkylenated units and, more advantageously, 1-20 oxyalkylenated units, that can form polyoxyalkylene, notably polyoxyethylene chains. These groups can be branches, at the end of the chain, or intended to link two parts of the silicone structure. The silicon atoms bearing these groups are approximately 1-10 in number.

Although the invention concerns more particularly organopolysiloxanes with oxyethylenated group(s), it can also concern the organopolysiloxanes with oxypropylenated group(s). The organopolysiloxanes can comprise simultaneously one or more oxyethylenated group(s), 1-20 (OE), for example, and one or more oxypropylenated group(s) (OP), 0-20, for example; these organopolysiloxanes are also called organopolysiloxanes with alkylethoxy-propylenated group(s). It is preferred for the number of oxyethylenated groups to be larger than the number of oxypropylenated groups.

As the partially or completely crosslinked organopolysiloxane comprising a polyoxyethylenated and/or polyoxypropylenated chain one can mention, for example, the product marketed by Shin-Etsu under the tradenames KSG21, KSG31, KSG31x and KSG32 or by Dow Corning under the name DC 9011. One can also mention the product of Example 3 of U.S. Pat. No. 5,412,004, containing approximately 33 wt % of organopolysiloxane and approximately 67 wt % of silicone oil having a viscosity of 6 cSt.

Also useful herein are polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin.

ii.) Solvent for the Emulsifying Crosslinked Siloxane Elastomer

The compositions of the present invention comprise a solvent for the emulsifying crosslinked organopolysiloxane elastomer described hereinbefore. The solvent, when combined with the cross-linked organopolysiloxane elastomer particles, serves to suspend and swell the elastomer particles to provide an elastic, gel-like network or matrix. The solvent for the emulsifying cross-linked siloxane elastomer is liquid under ambient conditions, and preferably has a low viscosity to provide for improved spreading on the skin. The viscosity of the elastomer gel is preferably greater than 100,000 cps, more preferably at least about 250,000 cps, optimally from about 300,000 to about 6,000,000 cps at 25° C. as measured by a Brookfield LV Viscometer (size 4 bar, 60 rpm, 0.3 sec.).

Concentrations of the solvent in the cosmetic compositions of the present invention will vary primarily with the type and amount of solvent and the emulsifying cross-linked siloxane elastomer employed. Preferred concentrations of the solvent are from about 10% to about 90%, preferably from about 20% to about 80%, more preferably from about 30% to about 70%, by weight of the composition.

The solvent for the emulsifying cross-linked siloxane elastomer comprises one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected emulsifying cross-linked siloxane elastomer at the selected siloxane elastomer concentration at a temperature of from about 28° C. to about 250° C., preferably from about 28° C. to about 100° C., preferably from about 28° C. to about 78° C. The solvent for the emulsifying cross-linked siloxane elastomer preferably has a solubility parameter of from about 3 to about 13 $(cal/cm^3)^{0.5}$, more preferably from about 5 to about 11 $(cal/cm^3)^{0.5}$, most preferably from about 5 to about 9 $(cal/cm^3)^{0.5}$. Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47-69, October 1988; and C. D. Vaughan, "Using Solubility Parameters in Cosmetics Formulation", 36 J. Soc. Cosmetic Chemists 319-333, September/October, 1988, which articles are incorporated herein by reference.

The solvent preferably includes volatile, non-polar oils; non-volatile, relatively polar oils; non-volatile, non-polar oils; and non-volatile paraffinic hydrocarbon oils; each discussed more fully hereinafter. The term "non-volatile" as used herein refers to materials which exhibit a vapor pressure of no more than about 0.2 mm Hg at 25° C. at one atmosphere and/or to materials which have a boiling point at one atmosphere of at least about 300° C. The term "volatile" as used herein refers to all materials that are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 $(cal/cm^3)^{0.5}$.

1. Non-Polar, Volatile Oils

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are selected from the group consisting of silicone oils; hydrocarbons; and mixtures thereof. Such non-polar, volatile oils are disclosed for example, in Cosmetics, Science, and Technology, Vol. 1, 27-104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons including polydecanes such as isododecane and isodecane (e.g., Permethyl-99A which is available from Presperse Inc.) and the C7-C8 through C12-C15 isoparaffins (such as the Isopar Series available from Exxon Chemicals). Nonpolar, volatile liquid silicone oils are disclosed in U.S. Pat. No. 4,781,917 issued to Luebbe et al. on Nov. 1, 1988, herein incorporated by reference in its entirety. Additionally, a description of various volatile silicones materials is found in Todd et al., "Volatile Silicone Fluids for Cosmetics", Cosmetics and Toiletries, 91:27-32 (1976), herein incorporated by reference in its entirety. Particularly preferred volatile silicone oils are selected from the group consisting of cyclic volatile silicones corresponding to the formula:

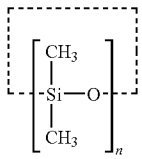

wherein n is from about 3 to about 7; and linear volatile silicones corresponding to the formula:

$(CH_3)_3Si\text{—}O\text{—}[Si(CH_3)_2\text{—}O]_m\text{—}Si(CH_3)_3$ wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G. E. Silicones), GE 7207 and 7158 (commercially available from General Electric Co.); and SWS-03314 (commercially available from SWS Silicones Corp.).

2. Relatively Polar, Non-Volatile Oils

The non-volatile oil is "relatively polar" as compared to the non-polar, volatile oil discussed above. Therefore, the non-volatile co-solvent is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989, all of which are herein incorporated by reference in their entirety. Relatively polar, non-volatile oils useful in the present invention are preferably selected from the group consisting of silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-solvents useful in the present invention may be either saturated or unsaturated, have an aliphatic character and be straight or branched chained or contain alicyclic or aromatic rings. More preferably, the relatively polar, non-volatile liquid co-solvent are selected from the group consisting of fatty alcohols having from about 12-26 carbon atoms; fatty acids having from about 12-26 carbon atoms; esters of monobasic carboxylic acids and alcohols having from about 14-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms and a degree of ethoxylation and propoxylation of below about 50; and mixtures thereof. More preferred are propoxylated ethers of C14-C18 fatty alcohols having a degree of propoxylation below about 50, esters of C2-C8 alcohols and C12-C26 carboxylic acids (e.g. ethyl myristate, isopropyl palmitate), esters of C12-C26 alcohols and benzoic acid (e.g. Finsolv TN supplied by Finetex), diesters of C2-C8 alcohols and adipic, sebacic, and phthalic acids (e.g., diisopropyl sebacate, diisopropyl adipate, di-n-butyl phthalate), polyhydric alcohol esters of C6-C26 carboxylic acids (e.g., propylene glycol dicaprate/dicaprylate, propylene glycol isostearate); and mixtures thereof. Even more preferred are branched-chain aliphatic fatty alcohols having from about 12-26 carbon atoms. Even more preferred is isocetyl alcohol, octyldecanol, octyldodecanol and undecylpentadecanol; and most preferred is octyldodecanol. Such preferred aliphatic fatty alcohols are particularly useful in combination with the volatile liquid silicone oils discussed herein to adjust the average solubility of the solvent.

3. Non-Polar, Non-Volatile Oils

In addition to the liquids discussed above, the solvent for the emulsifying cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. Both of which are herein incorporated by reference. The non-volatile oils useful in the present invention are essentially non-volatile polysiloxanes, paraffinic hydrocarbon oils, and mixtures thereof. The polysiloxanes useful in the present invention selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 1 to about 100,000 centistokes at 25° C. Among the preferred non-volatile silicone emollients useful in the present compositions are the polydimethyl siloxanes having viscosities from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991, herein incorporated by reference in its entirety. Preferred mineral oils have the following properties:

(1) viscosity from about 5 centistokes to about 70 centistokes at 40° C.;

(2) density between about 0.82 and 0.89 g/cm3 at 25° C.;

(3) flash point between about 138° C. and about 216° C.; and (4) carbon chain length between about 14 and about 40 carbon atoms.

Preferred branched chain hydrocarbon oils have the following properties:
(1) density between about 0.79 and about 0.89 g/cm3 at 20° C.
(2) boiling point greater than about 250° C.; and
(3) flash point between about 110° C. and about 200° C.

Particularly preferred branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

When used herein, volatile or non-volatile hydrocarbon oils are preferably present at concentrations less than 30%, more preferably, from about 1% to about 25%, most preferably from about 1% to about 15%.

Additional solvents useful herein are described in U.S. Pat. No. 5,750,096 to Gerald J. Guskey et al., issued May 12, 1998, herein incorporated by reference in its entirety.

B. The Discontinuous Phase of the Emulsion Composition

Another essential component of the present invention is the discontinuous phase. The discontinuous phase is, preferably, composed of non-oily or aqueous materials. Suitable non-oily or aqueous materials include, but are not limited to polyhydric alcohols (polyols) or water. Examples of polyhydric alcohols include polyalkylene glycols and more preferably alkylene polyols and their derivatives. Illustrative are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. Most preferably the polyhydric alcohol is glycerin.

The discontinuous phase, preferably, forms droplets having a droplet size distribution range of from about 0.1 microns to about 100 microns. More preferably the discontinuous phase droplets have a droplet size distribution range such that at least 20%, preferably 15%, more preferably 10% of the droplets have a droplet size of greater than 40 microns, more preferably greater than 60 microns, most preferably greater than 75 microns, and optimally greater than 40 microns.

The discontinuous phase preferably comprises from 1 to 95%, more preferably 1 to 50%, most preferably from 10 to 40%, optimally from 25 to 35% by weight.

An essential component of the discontinuous phase are solid particles. Suitable solid particles include, but are not limited to ingredients which may be compounded in the composition of the present invention include inorganic powder such as gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as ethylene acrylate, latex, polyamide resin powder (nylon powder), cyclodextrin, polyethylene powder, methyl polymethacrylate powder, polystyrene powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as titanium dioxide, zinc oxide, and magnesium oxide. Other useful powders are disclosed in U.S. Pat. No. 5,688,831, to El-Nokaly et al., issued Nov. 18, 1997, herein incorporated by reference in its entirety.

Preferred organic powders/fillers include, but are not limited to, polymeric particles chosen from the methylsilsesquioxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyrene microspheres such as for example those sold by Dyno Particles under the name Dynospheres, ethylene acrylate copolymer sold by Kobo under the name FloBead EA209 and mixtures thereof.

Also useful herein are pigment and/or dye encapsulates such nanocolorants from BASF and multi-layer interference pigments such as Sicopearls from BASF.

Mixtures of the above powders may also be used.

Preferably the powders of the present invention have a particle size such that the average chord length of the powder particles range from about 0.01 microns to about 100 microns, preferably from about 0.1 microns to about 50 microns, more preferably from about 1 micron to about 20 microns.

Preferably the solid particles comprise from about 0.01% to about 30%, more preferably from about 1% to about 20%, most preferably from about 5% to about 15% by weight of the multi-phase emulsion compositions.

Optional Ingredients

Skin Conditioning Agent

Optionally, the compositions of the present invention can further comprise a skin conditioning agent. These agents may be selected from exfoliants or emollients.

Exfoliants according to the present invention may be selected from C2-C30 alpha-hydroxycarboxylic acids, beta-hydroxycarboxylic acids and salts of these acids. Most preferred are glycolic, lactic and salicylic acids and their ammonium salts. Amounts of the exfoliants may range from 1 to 15%, preferably from 2 to 10% by weight.

A wide variety of C2-C30 alpha-hydroxycarboxylic acids may be employed. Suitable examples of which include:
alpha-hydroxyethanoic acid
alpha-hydroxypropanoic acid
alpha-hydroxyhexanoic acid
alpha-hydroxyoctanoic acid
alpha-hydroxydecanoic acid
alpha-hydroxydodecanoic acid
alpha-hydroxytetradecanoic acid
alpha-hydroxyhexadecanoic acid
alpha-hydroxyoctadecanoic acid alpha-hydroxyeicosanoic acid
alpha-hydroxydocosanoic acid
alpha-hydroxyhexacosanoic acid, and
alpha-hydroxyoctacosanoic acid When the conditioning agent is an emollient it may be selected from hydrocarbons, fatty acids, fatty alcohols and esters. Isononyl isononanoate is the most preferred hydrocarbon type of emollient conditioning agent. Other hydrocarbons that may be employed include mineral oil, polyolefins such as polydecene, and paraffins such as isohexadecane (e.g. Permethyl 99 Registered™ and Permethyl 101 Registered™). Preferably, the compositions of the present invention are substantially free of semi-solid hydrocarbons such as petrolatum, lanolin and lanolin derivatives, sterols (e.g., ethoxylated soya sterols), high molecular weight polybutenes and coco butter. By "substantially free," as used herein, means that the concentration of the semi-solid hydrocarbons are preferably less than 10%, more preferably less than 5% most preferably less than 2% and even more preferably 0. Without being limited by theory, such semi-solid hydrocarbons tend to mask the sensory benefits of the siloxane elastomer compositions such as the non-greasy, light feel of the present invention.

Fatty acids and alcohols will have from 10 to 30 carbon atoms. Illustrative of this category are pelargonic, lauric, myristic, palmitic, stearic, isostearic, hydroxystearic, oleic, linoleic, ricinoleic, arachidic, behenic and erucic acids and alcohols.

Oily ester emollients may be those selected from one or more of the following classes:

1. Triglyceride esters such as vegetable and animal fats and oils. Examples include castor oil, cocoa butter, safflower oil, cottonseed oil, corn oil, olive oil, cod liver oil, almond oil, avocado oil, palm oil, sesame oil, squalene, Kikui oil and soybean oil.

2. Acetoglyceride esters, such as acetylated monoglycerides.

3. Ethoxylated glycerides, such as ethoxylated glyceryl monostearate.

4. Alkyl esters of fatty acids having 10 to 20 carbon atoms. Methyl, isopropyl, and butyl esters of fatty acids are useful herein. Examples include hexyl laurate, isohexyl laurate, isohexyl palmitate, isopropyl palmitate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate.

5. Alkenyl esters of fatty acids having 10 to 20 carbon atoms. Examples thereof include oleyl myristate, oleyl stearate, and oleyl oleate.

6. Ether-esters such as fatty acid esters of ethoxylated fatty alcohols.

7. Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol polyfatty esters, ethoxylated glyceryl monostearate, 1,2-butylene glycol monostearate, 1,2-butylene glycol distearate, polyoxyethylene polyol fatty acid ester, sorbitan fatty acid esters, and polyoxyethylene sorbitan fatty acid esters are satisfactory polyhydric alcohol esters.

8. Wax esters such as beeswax, spermaceti, myristyl myristate, stearyl stearate.

9. C1-C30 mono- and poly-esters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoleate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 1:3 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7-8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. Nos. 2,831,854, 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Amounts of the skin conditioning agent may range from about 0% to 30%, preferably from about 1% to about 20%, optimally from about 1% to 10% by weight.

Solidifying Agent

The cosmetic compositions of this invention can contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition which has a stable physical structure and is deposited on the skin during normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent is preferably present at a concentration of from about 0 to about 90%, more preferably from about 1 to about 50%, even more preferably from about 5% to about 40%, most preferably from about 1% to about 15%.

Suitable solidifying agents include waxy materials such as candelilla, carnauba waxes, beeswax, spermaceti, carnauba, baysberry, montan, ozokerite, ceresin, paraffin, synthetic waxes such as Fisher-Tropsch waxes, silicone waxes (e.g., DC 2503 from Dow Corning), microcrystalline waxes and the like; soaps, such as the sodium and potassium salts of higher fatty acids, i.e., acids having from 12 to 22 carbon atoms; amides of higher fatty acids; higher fatty acid amides of alkylolamines; dibenzaldehyde-monosorbitol acetals; alkali metal and alkaline earth metal salts of the acetates, propionates and lactates; and mixtures thereof. Also useful are polymeric materials such as, locust bean gum, sodium alginate, sodium caseinate, egg albumin, gelatin agar, carrageenin gum sodium alginate, xanthan gum, quince seed extract, tragacanth gum, starch, chemically modified starches and the like, semi-synthetic polymeric materials such as cellulose ethers (e.g. hydroxyethyl cellulose, methyl cellulose, hydroxypropyl cellulose, carboxymethyl cellulose, hydroxy propylmethyl cellulose), polyvinylpyrrolidone, polyvinylalcohol, guar gum, hydroxypropyl guar gum, soluble starch, cationic celluloses, cationic guars and the like and synthetic polymeric materials such as carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers and the like. Inorganic thickeners may also be used such as aluminium silicates, such as, for example, bentonites, or a mixture of polyethylene glycol and polyethylene glycol stearate or distearate. Naturally occurring polymers or biopolymers and their use are further described in European Application No. 522624, to Dunphy et al. Additional examples of naturally occurring polymers or biopolymers can be found in the Cosmetic Bench Reference, pp. 1.40-1.42, herein incorporated by reference.

Also useful herein are hydrophilic gelling agents such as the acrylic acid/ethyl acrylate copolymers and the carboxyvinyl polymers sold by the B.F. Goodrich Company under the trademark of Carbopol Registered™ resins. These resins consist essentially of a colloidally water-soluble polyalkenyl polyether crosslinked polymer of acrylic acid crosslinked with from 0.75% to 2.00% of a crosslinking agent such as polyallyl sucrose or polyallyl pentaerythritol. Examples include Carbopol 934, Carbopol 940, Carbopol 950, Carbopol 980, Carbopol 951 and Carbopol 981. Carbopol 934 is a water-soluble polymer of acrylic acid crosslinked with about 1% of a polyallyl ether of sucrose having an average of about 5.8 allyl groups for each sucrose molecule. Also suitable for use herein are carbomers sold under the Trade Name "Carbopol Ultrez 10, Carbopol ETD2020, Carbopol 1382, Carbopol 1342 and Pemulen TR-1 (CTFA Designation: Acrylates/10-30 Alkyl Acrylate Crosspolymer). Combination of the above polymers are also useful herein. Other gelling agents suitable for use herein include oleogels such as trihydroxystearin.

Hydrophobically modified celluloses are also suitable for use herein. These celluloses are described in detail in U.S. Pat. Nos. 4,228,277 and 5,104,646, both of which are herein incorporated by reference in their entirety.

Additional examples of suitable gelling agents or gellants can be found in the Cosmetic Bench Reference, p. 1.27, herein incorporated by reference.

Further examples of suitable solidifying agents disclosed in the following references, all of which are incorporated by reference herein: U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981; "The Chemistry and Technology of Waxes", A. H. Warth, 2nd Edition, reprinted in 1960, Reinhold Publishing Corporation, pp 391-393 and 421; "The Petroleum Chemicals Industry", R. F. Goldstein and A. L. Waddeam, 3rd Edition (1967), E & F. N. Span Ltd., pp 33-40; "The Chemistry and Manufacture of Cosmetics", M. G. DeNavarre, 2nd edition (1970), Van Nostrand & Company, pp 354-376; and in "Encyclopedia of Chemical Technology: Vol. 24, Kirk-Othmer, 3rd Edition (1979) pp 466-481; U.S. Pat. No. 4,126,679, Davy, et al., issued Nov. 21, 1978; European Patent Specification No. 117,070, May, published Aug. 29, 1984; U.S. Pat. No. 2,900,306, Slater, issued Aug. 18, 1959; U.S. Pat. No. 3,255,082, Barton, issued Jun. 7, 1966; U.S. Pat. No. 4,137, 306, Rubino, et al., issued Jan. 30, 1979; U.S. Pat. No. 4,154, 816, Roehl, et al., issued May 15, 1979; U.S. Pat. No. 4,226, 889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; European Patent Specification No. 107,330, Luebbe, et al., published May 2, 1984; European Patent Specification No. 24,365 Sampson, et al., published Mar. 4, 1981; and U.S. patent application Ser. No. 630,790, DiPietro, filed Jul. 13, 1984.

Preferably, the compositions of the present invention have a hardness value as measured using a TA-XT2i Texture Analyzer (described below) of up to about 25 gram-force, more preferably from about 0.5 to about 20 gram-force, most preferably from about 1 to about 15, optimally from about 1 to about 10 gram-force. Without being limited by theory, it is believed that compositions having stick hardness values above 25 gram-force tend to interfere with the formation of the film structure provided by the polysiloxane elastomer, thus, preventing the smoothness as well as improved uniformity and evenness of particle distribution within the film. This, in turn, negatively affects the sensory benefits of the cross-linked polysiloxane elastomer component.

Colorant

Certain embodiments of the present invention contain from about 0% to about 30%, preferably from about 1% to about 20%, more preferably from about 2% to about 15% and most preferably from about 5% to about 15%, of a non-pigment colorant, on an anhydrous weight basis. These are usually aluminum, barium or calcium salts or lakes. Preferably, dyes are present at from about 0% to about 3% and pearls and the like from 0% to about 10%.

Colorants useful herein are all inorganic and organic colors suitable for use in cosmetic compositions.

Lakes are either a pigment that is extended or reduced with a solid diluent or an organic pigment that is prepared by the precipitation of a water-soluble dye on an adsorptive surface, which usually is aluminum hydrate. There is uncertainty in some instances as to whether the soluble dye precipitates on the surface of the aluminum hydrate to yield a dyed inorganic pigment or whether it merely precipitates in the presence of the substrate. A lake also forms from precipitation of an insoluble salt from an acid or basic dye. Calcium and barium lakes are also used herein.

Lakes suitable for use in the present invention include Red 3 Aluminum Lake, Red 21 Aluminum Lake, Red 27 Aluminum Lake, Red 28 Aluminum Lake, Red 33 Aluminum Lake, Yellow 5 Aluminum Lake, Yellow 6 Aluminum Lake, Yellow 10 Aluminum Lake, Orange 5 Aluminum Lake and Blue 1 Aluminum Lake, Red 6 Barium Lake, Red 7 Calcium Lake.

Other colors can also be included herein, such as dyes. Suitable examples include Red 6, Red 21, Brown, Russet and Sienna dyes and mixtures thereof.

Preservatives

Suitable traditional preservatives for compositions of this invention are alkyl esters of para-hydroxybenzoic acid. Other preservatives which have more recently come into use include hydantoin derivatives such as 1,3-bis(hydroxymethyl)-5,5-dimethylhydantoin, propionate salts, and a variety of quaternary ammonium compounds such as benzalkonium chloride, quaternium 15 (Dowicil 200), benzethonium Chloride, and methylbenzethonium chloride. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives preferably are employed in amounts ranging from about 0% to about 5%, more preferably from about 0.01% to about 2.5%, and most preferably from about 0.01% to about 1%, by weight of the composition.

Emulsifiers

Emulsifiers or surfactants can also be used herein. These emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986), each incorporated herein by reference in its entirety. Illustrative nonionic surfactants are alkoxylated compounds based on C10-C22 fatty alcohols and acids, and sorbitan. These materials are available, for instance, from the Shell Chemical Company under the Neodol trademark, Copolymers of polyoxypropylene-polyoxyethylene, sold by the BASF Corporation under the Pluronic trademark, are sometimes also useful. Alkyl polyglycosides available from the Henkel Corporation may also be utilized for purposes of this invention. Anionic type emulsifiers or surfactants include fatty acid soaps, sodium lauryl sulphate, sodium lauryl ether sulphate, alkyl benzene sulphonate, mono- and di-alkyl acid phosphates and sodium fatty acyl isethionate. Amphoteric emulsifiers or surfactants include such materials as dialkylamine oxide and various types of betaines (such as cocamidopiopyl betaine).

Preferred for use herein are polyoxyalkylene copolymers also known as silicone polyethers. Polymers are described in detail in U.S. Pat. No. 4,268,499, which is incorporated herein by reference in its entirety. A particularly preferred polyoxyalkylene copolymer is known by its CTFA designation as dimethicones copolyol. A particularly preferred form of dimethicone copolyol is that supplied by Dow Corning as DC5225C.

The overall concentration of the emulsifier can be from 0% to about 10% of the formulation, preferably from 0.1% to about 5% and most preferably from about 0.1% to about 2%, by weight of the composition. Examples of suitable emulsifiers can be found in U.S. Pat. No. 5,085,856 to Dunphy et al.; Japanese Patent Publication Sho 61-83110; European Patent Application EP 522624 to Dunphy et al.; U.S. Pat. No. 5,688,831 to El-Nokaly et al.; and Examples of suitable moistures can be found in Cosmetic Bench Reference, pp. 1.22, 1.24-1.26 (1996), all of which are herein incorporated by reference in their entirety.

Aerated Compositions

Optionally and preferably, the compositions of the present invention are aerated. By "aerated" as used herein means the air is incorporated either by hand, mechanical mixing or by using any other form of conventional foaming or whipping instrument technology. Preferably the compositions of the present invention contain at least about 1%, preferably at least about 2%, optimally from about 3 to about 5% air.

Other Optional Ingredients

A variety of additional ingredients can be incorporated into the compositions of the present invention. Nonlimiting examples of these additional ingredients include additional skin care actives such as peptides (e.g., Matrixyl [pentapetide derivative]), farnesol, bisabolol, phytantriol, glycerol, urea, guanidine (e.g., amino guanidine); vitamins and derivatives thereof such ascorbic acid, vitamin A (e.g., retinoid derivatives such as retinyl palmitate or retinyl proprionate), vitamin E (e.g., tocopherol acetate), vitamin $B_3$ (e.g., niacinamide) and vitamin $B_5$ (e.g., panthenol) and the like and mixtures thereof; sunscreens; anti-acne medicaments (resorcinol, salicylic acid, and the like; antioxidants (e.g., phytosterols, lipoic acid); flavonoids (e.g., isoflavones, phytoestrogens); skin soothing and healing agents such as aloe vera extract, allantoin and the like; chelators and sequestrants; and agents suitable for aesthetic purposes such as essential oils, fragrances, skin sensates, opacifiers, aromatic compounds (e.g., clove oil, menthol, camphor, eucalyptus oil, and eugenol). Nonlimiting examples of suitable carboxylic copolymers, emulsifiers, emollients, and other additional ingredients are disclosed in U.S. Pat. No. 5,011,681, to Ciotti et al., issued Apr. 30, 1991 and U.S. Pat. No. 5,939,082, to Oblong et al., issued Aug. 17, 1999, both of which are herein incorporated by reference. The above mentioned vitamin $B_3$ compounds can be incorporated as re-crystallized crystals which remain in crystallized form in the composition or as partially solubilize crystals (i.e., some of the crystals are dissolved and some remain in crystalline form in the composition.).

Analytical Test Methods

Hardness Value Test

The term "product hardness" as used herein is a reflection of how much force is required to move a rod a specified distance and at a controlled rate into a cosmetic composition under the following test conditions. Higher values represent harder product, and lower values represent softer product. These values are measured at 27° C., 15% relative humidity, using a TA-XT2i Texture Analyzer, available from Texture Technology Corp., Scarsdale, N.Y., U.S.A. The product hardness value as used herein represents the amount of force required to move a 16 mm long stainless steel rod having a 0.254 mm diameter through the composition for a distance of 12.2 mm at a rate of 0.85 mm/second. The rod is attached to the instrument by means of a suitable adapter (e.g., drill-type chuck). Other test parameters include: Pre-Test Speed of 0.85 mm/s, Post Test Speed of 1.70 mm/s, trigger distance of 0.1 mm. More detailed instructions can be found in the Operator's Manuel for the TA-XT2i, herein incorporated by reference.

The following examples will more fully illustrate the embodiments of this invention. All parts, percentages and proportions referred to herein and in the appended claims are by weight unless otherwise indicated.

EXAMPLES

The cosmetic products in the following examples illustrate specific embodiments of the cosmetic compositions of the present invention, but are not intended to be limiting thereof. Other modifications can be undertaken by the skilled artisan without departing from the spirit and scope of this invention. All exemplified compositions can be prepared by conventional formulation and mixing techniques. Component amounts are listed as weight percents and may exclude minor materials such as diluents, filler, and so forth. The listed formulations, therefore, comprise the listed components and any minor materials associated with such components.

Example I

A lipstick composition of the present invention is prepared as follows:

| Ingredient | |
|---|---|
| Carnauba | 1.50 |
| Ozokerite | 5.50 |
| Candelillia | 4.00 |
| Hydrogenated Vegetable Oil | 8.50 |
| Acetylated Lanolin | 4.00 |
| Propylparaben | 0.10 |
| Cetyl Ricinoleate | 10.00 |
| Ascorbyl Palmitate | 1.00 |
| Polybutene | 2.00 |
| Polysiloxane Copolymer[1] | 5.97 |
| Stearyl Dimethicone (DC 2503 Cosmetic wax) | 5.97 |
| Anhydrous Lanolin | 5.97 |
| KSG 21[2] Elastomer gel | 22.95 |
| Association Structure Phase | |
| Lecithin | 5.00 |
| Niacinamide | 2.50 |
| Panthenol | 1.00 |
| Glycerine | 4.04 |
| Pigment | 9.00 |
| water | 6.00 |

[1] #1154-141-1, supplied by GE Silicones.
[2] 25% Dimethicone/copolyol Crosspolymer in dimethicone.

The ingredients for the Association Structure Phase, except for the pigments, are mixed until association structures are formed. Once the association structures are formed, the pigments are added and milled on a three roll mill. The mixture is then mixed with the remaining ingredients and mixed until a homogeneous mixture. (Or, alternatively, the above components are added and mixed together at the same time.) This mixture is heated to 85° C. and then poured into a mold at room temperature.

The lipstick is applied to the lips to provide color, moisturization and improved lip feel.

Example II

A mascara of the present invention is prepared as follows:

| Ingredient | Wt. % |
|---|---|
| Carnauba Wax | 3.00 |
| Glyceryl Monostearate[1] | 7.50 |
| White Beeswax | 3.75 |
| C18-C36 Triglycerides[2] | 5.50 |
| Hydrogenated Glycerol Rosinate[3] | 0.15 |
| Propylparaben | 0.10 |
| Paraffin Wax 118/125 | 2.25 |
| Paraffin Wax | 2.25 |
| Elastomer Gel (KSG21)[4] | 17.31 |
| Lecithin[5] | 2.25 |
| Stearic Acid 3X | 4.00 |
| Oleic Acid | 0.75 |
| Triethanolamine | 1.25 |
| Potassium Cetyl Phosphate[6] | 1.00 |
| Shellac, NF | 3.00 |
| Triethanolamine | 0.47 |
| Trisodium EDTA | 0.10 |
| Black Iron Oxide | 7.00 |

-continued

| Ingredient | Wt. % |
|---|---|
| Simethicone | 0.20 |
| Methylparaben | 0.20 |
| Ethylparaben | 0.15 |
| Phenoxyethanol | 0.80 |
| Ethyl Alcohol 40B, 190 proof | 4.00 |
| Diazolidinyl Urea | 0.20 |
| Deionized Water | 30.22 |
| dl-Panthenol | 0.35 |
| niacinamide | 2.25 |
| Total | 100.00 |

[1] Available as Emerest 2400 available form Henkel/Emery-
[2] Available as Syncrowax HGL-C available from Croda, Inc.-
[3] Available as Foral 105 available from Hercules, Inc.-
[4] 25% Dimethicone/Copolyol Crosspolymer in dimethicone
[5] Available as Centrolex F available from Central Soya, Inc.-
[6] Available as Amphisol K available from Givaudan- The waxes and fats are mixed in a vessel equipped with a heating source. The waxes and fats are heated and mixed at low speed using a conventional blender to liquify the mixture. The mixing is continued until the mixture is homogeneous. To the homogenous mixture is added the pigments. The mixing rate is increased to high and the pigments are mixed into the mixture for about 30-35 minutes until uniformly dispersed. The mixing is continued while adding emulsifiers.

In a second vessel equipped with a heating source is added water followed by the niacinamide, lecithin and any other water-dispersable components. The mixture is heated and mixed to a temperature of from about 80-95° C. Additional water is added as necessary to account for water loss.

The aqueous and lipophilic mixtures are combined and mixed using a dispersator type mixer. Mixing is continued until the mixture cools to a temperature of from about 65-70° C. Preservatives are added with mixing, allowing the mixture to cool further to 45-47° C. Any remaining components are added with mixing. The combined mixture is cooled to a temperature above the solidification point and is then poured into suitable containers.

The mascara composition is applied to the lashes and/or eyebrows to provide softening, moisturization and conditioning.

Example III

A moisturizing lotion of the present invention is prepared as follows:

| Raw Material | Weight % |
|---|---|
| Cyclomethicone (DC245) | 20.35 |
| Elastomer Gel (KSG21)[1] | 33.33 |
| Propylparaben | 0.20 |
| Ethylene/Acrylic Acid Copolymer microspheres (Flobeads EA 209 supplied by Kobo Products Inc.) | 10.00 |
| Glycerin | 25.00 |
| Water | 8.00 |
| Niacinamide | 3.00 |
| Methylparaben | 0.12 |
| Total = | 100.00 |

[1] 25% Dimethicone/Copolyol Crosspolymer in dimethicone

In a suitable stainless steel vessel, the cyclomethicone, KSG21 and propylparaben are added with mixing using conventional mixing technology and mixed until homogeneous.

In a separate vessel, the niacinamide and water are mixed using conventional mixing technology until homogeneous. To the niacinamide solution is next added the glycerin, ethylene/acrylic acid copolymer microspheres and methylparaben with mixing until homogeneous. Next, the niacinamide mixture is combined with the cyclomethicone mixture and mixed using conventional mixing technology until homogeneous. The combined mixture is then poured into suitable containers.

The moisturizing cosmetic lotion is applied to the face and/or body to provide softening, moisturization and conditioning.

Example IV

A liquid foundation of the present invention is prepared as follows:

| Ingredient | Weight % |
| --- | --- |
| Cyclomethicone | 12.32 |
| KSG32 Elastomer Gel[1] | 15.38 |
| Isononyl Isononanoate | 5.00 |
| n-Propyl-4-hydroxybenzoic Acid | 0.20 |
| Ethylene Brassylate | 0.03 |
| Titanium Dioxide | 17.8 |
| Yellow Iron Oxide | 1.70 |
| Red Iron Oxide | 0.19 |
| Black Iron Oxide | 0.11 |
| Methylparahydroxybenzoate | 0.12 |
| Glycerin | 10.00 |
| 2-amino-2-methyl-1-propanol | 0.10 |
| Water | 36.45 |
| sucrose oleate ester | 0.60 |
| | 100.00 |

[1] 25%% Lauryl Dimethicone/Copolyol Crosspolymer in isododecane

In a suitable stainless steel vessel, the cyclomethicone, KSG32, isononyl isononanoate, n-propyl-4-hydroxybenzoic acid, and ethylene brassylate are added with mixing using conventional mixing technology and mixed until homogeneous. In a separate vessel equipped with a heat source, the sucrose oleate ester and water are heated to 50° C. and mixed using conventional mixing technology until homogeneous. The sucrose oleate ester mixture is then allowed to cool to room temperature. Once cooled, the titanium dioxide, iron oxides, methylparahydroxy benzoate, glycerin and 2-amino-2-methyl-1-propanol are added to sucrose oleate ester mixture with mixing to form a homogeneous, pigment slurry. Next, the sucrose oleate ester mixture is combined with the cyclomethicone mixture and mixed using conventional mixing technology until homogeneous. The combined mixture is then poured into suitable containers.

The liquid foundation is applied to the face to provide softening, moisturization and conditioning.

What is claimed is:

1. A stable multiphase emulsion composition, comprising:
   A.) from 1 to 95% of a continuous phase, comprising:
      i.) from about 1% to about 50% of an emulsifying crosslinked siloxane elastomer; and
      ii.) from about 10% to about 90% of a solvent for the emulsifying crosslinked siloxane elastomer;
   B.) from 1 to 95% of at least one discontinuous phase, comprising:
      i.) solid particles
   wherein the discontinuous phase has a droplet size distribution range of from about 0.1 microns to about 100 microns, wherein at least 10% of the droplets are greater than 40 microns, and wherein the particles are uniformly distributed on the skin independent of skin topography.

2. The cosmetic composition of claim 1 wherein said composition further comprises a skin conditioning agent selected from the group consisting of exfoliants, emollients and mixtures thereof.

3. The cosmetic composition of claim 1 wherein said discontinuous phase is selected from the group consisting of polyhydric alcohol, water and mixtures thereof.

4. The cosmetic composition of claim 3 wherein said polyhydric alcohol is selected from the group consisting of propylene glycol, dipropylene glycol, polypropylene glycol, polyethylene glycol, sorbitol, hydroxypropyl sorbitol, hexylene glycol, glycerin, 1,3-butylene glycol, 1,2,6-hexanetriol, ethoxylated glycerin, propoxylated glycerin and mixtures thereof.

5. The cosmetic composition of claim 1 wherein said composition further comprises an emulsifier.

6. The cosmetic composition of claim 5 wherein said emulsifier is polyoxyalkylene copolymer.

7. The cosmetic composition of claim 6 wherein said polyoxyalkylene copolymer is dimethicone copolyol.

8. The cosmetic composition of claim 1 wherein said solid is selected from the group consisting of inorganic solid particles, organic solid particles and mixtures thereof.

9. The cosmetic composition of claim 8 wherein said solid particle is selected from the group consisting of gums, chalk, Fuller's earth, talc, kaolin, iron oxide, mica, sericite, muscovite, phlogopite, synthetic mica, lepidolite, biotite, lithia mica, vermiculite, magnesium carbonate, calcium carbonate, aluminum silicate, starch, smectite clays, alkyl and/or trialkyl aryl ammonium smectites, chemically modified magnesium aluminum silicate, organically modified montmorillonite clay, hydrated aluminum silicate, fumed silica, aluminum starch, octenyl succinate barium silicate, calcium silicate, magnesium silicate, strontium silicate, metal tungstate, magnesium, silica alumina, zeolite, barium sulfate, calcined calcium sulfate, calcium phosphate, fluorine apatite, hydroxyapatite, ceramic powder, metallic soap, colloidal silicone dioxide, boron nitride; polyamide resin powder, cyclodextrin, polyethylene powder, methyl polymethacrylate powder, polystyrene powder, copolymer powder of styrene and acrylic acid, benzoguanamine resin powder, poly(ethylene tetrafluoride) powder, carboxyvinyl polymer, cellulose powder, ethylene glycol monostearate, titanium dioxide, zinc oxide, magnesium oxide, interference pigments, and mixtures thereof.

10. The cosmetic composition of claim 1 wherein said composition further comprises a preservative.

11. The cosmetic composition of claim 10 wherein said preservative is selected from the group consisting of disodium EDTA, phenoxyethanol, methyl paraben, propyl paraben, imidazolidinyl urea, sodium dehydroacetate, para-hydroxybenzoic acid, hydantoin, propionate salts, quaternary ammonium compounds, benzyl alcohol, and mixtures thereof.

12. The cosmetic composition of claim 1 wherein said composition further comprises fillers.

13. The cosmetic composition of claim 1 wherein said composition is in the form of a foundation, mascara, concealer, eye liner, brow color, eye shadow, blusher, lip cream, lip gloss, lip paint or lipstick.

* * * * *